(12) United States Patent
Popescu et al.

(10) Patent No.: US 7,738,632 B2
(45) Date of Patent: Jun. 15, 2010

(54) X-RAY TUBE WITH TRANSMISSION ANODE

(75) Inventors: Stefan Popescu, Erlangen (DE); Georg Wittmann, Herzogenaurach (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 12/238,899

(22) Filed: Sep. 26, 2008

(65) Prior Publication Data

US 2009/0086918 A1    Apr. 2, 2009

(30) Foreign Application Priority Data

Sep. 27, 2007   (DE) .................. 10 2007 046 278

(51) Int. Cl.
*H01J 35/06* (2006.01)
(52) U.S. Cl. .................. 378/136; 378/124; 378/137
(58) Field of Classification Search .......... 378/119–144
See application file for complete search history.

(56) References Cited

U.S. PATENT DOCUMENTS

| 6,516,048 B2 * | 2/2003 | Mori .................. 378/119 |
| 7,180,981 B2 | 2/2007 | Wang |
| 2005/0175151 A1 * | 8/2005 | Dunham et al. .............. 378/122 |
| 2006/0098783 A1 * | 5/2006 | Dunham et al. .............. 378/122 |
| 2006/0115051 A1 | 6/2006 | Harding |
| 2007/0274454 A1 * | 11/2007 | Freudenberger et al. .... 378/136 |

FOREIGN PATENT DOCUMENTS

| DE | 27 29 833 | 1/1979 |
| DE | 10 2005 018 342 A1 | 11/2006 |
| EP | 0 147 009 | 12/1989 |

* cited by examiner

*Primary Examiner*—Hoon Song
(74) *Attorney, Agent, or Firm*—Schiff Hardin LLP

(57) ABSTRACT

An x-ray tube has a cathode that generates free electrons; an anode on which the free and accelerated electrons strikes so that x-ray radiation is generated; a cooling channel with coolant flowing therethrough to cool the anode; a vacuum region between the cathode and the anode; and an exit window through which the x-ray radiation exits from the x-ray tube. The anode is fashioned as a transmission anode; with the transmission anode arranged between the vacuum region and the cooling channel, with the cooling channel arranged between the transmission anode and the exit window; so the useful x-ray radiation passes through the coolant.

16 Claims, 2 Drawing Sheets

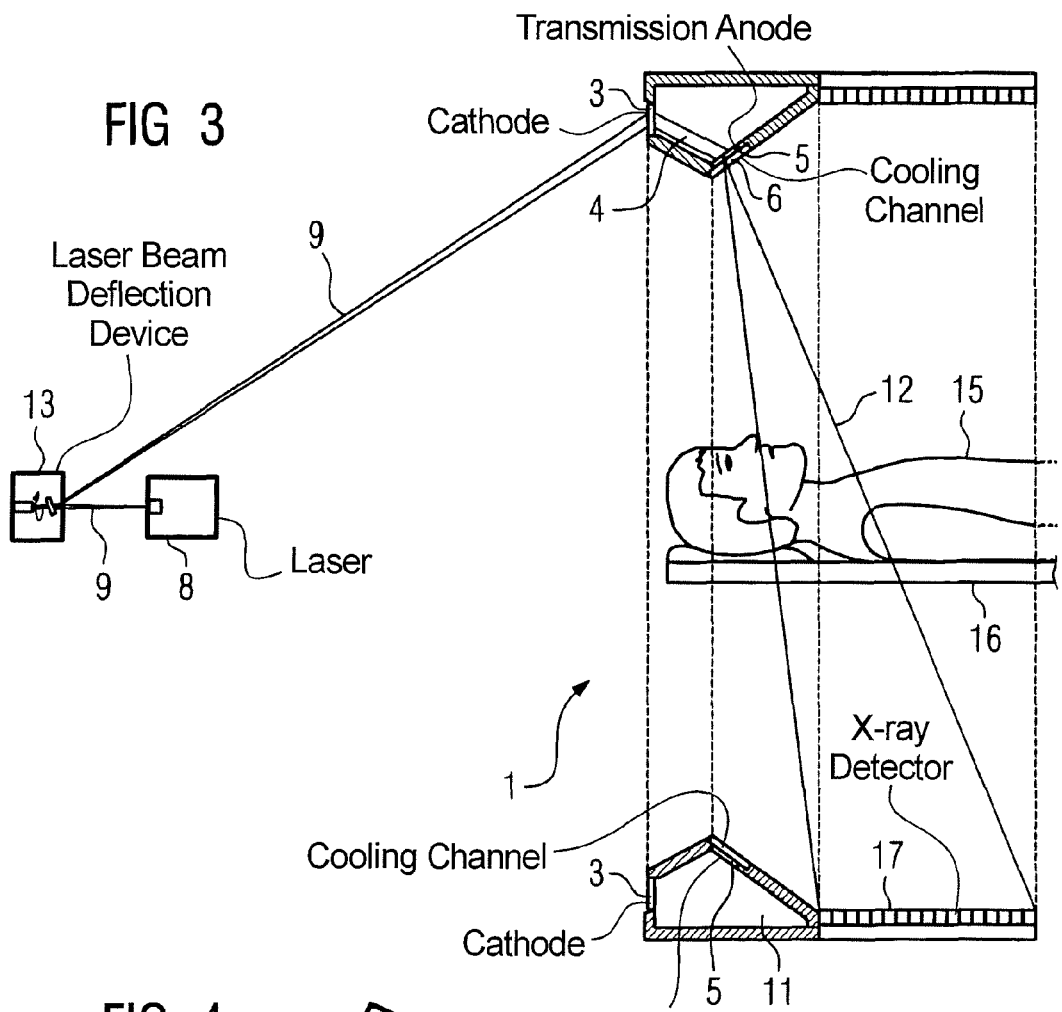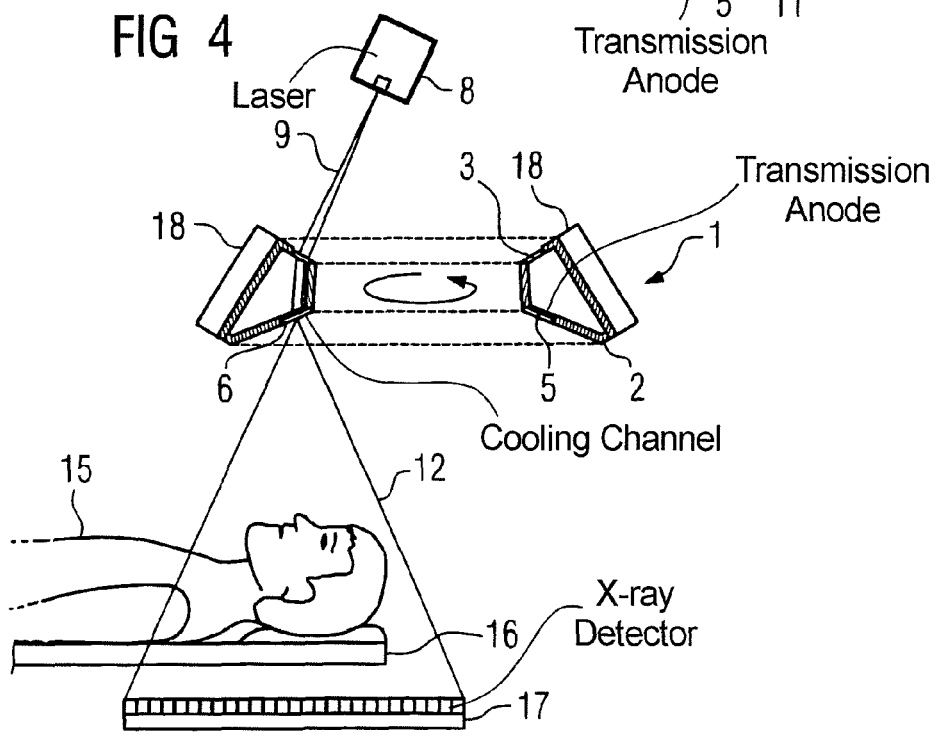

X-RAY TUBE WITH TRANSMISSION ANODE

BACKGROUND OF THE INVENTION

1. Field of the Invention

The invention concerns an x-ray tube of the type having a cathode to generate free electrons; an anode on which the free and accelerated electrons strike to cause x-ray radiation to be generated; a cooling channel with coolant flowing therethrough to cool the anode; a vacuum region between cathode and anode; and an exit window for allowing the x-ray radiation to exit from the x-ray tube.

2. Description of the Prior Art

An x-ray tube of this general type is known from United States Patent Application Publication 2006/015051 A1, for example. In this document an x-ray tube is disclosed in which a thin metal foil is used on which the electrons coming from a cathode (thus an electron source) strike with high energy and generate x-ray radiation that is directed out through a vacuum window. The thin cathode foil is cooled with the aid of a liquid. The foil is cooled on the back side, or the side facing away from the utilized radiation by a liquid conducted past the foil. A constriction in the cooling channel is present in the region of the cathode foil that leads to a higher flow speed of the liquid in this region so as to increase the effectiveness of the cooling. The quantity of generated bremsstrahlung is shifted relative to the generated characteristic radiation by this use of a very thin anode foil, such that an essentially monochromatic x-ray radiation arises in the range of the characteristic lines.

Although a relatively high degree of effectiveness is achieved in the generation of x-ray radiation in this embodiment of an x-ray tube, this is still not sufficient.

SUMMARY OF THE INVENTION

An object of the invention is to provide an x-ray tube that exhibits an improved efficiency between utilized radiation and expended energy.

The invention is based on the insight that the image quality of a computed tomograph apparatus is primarily determined by the quality of the x-ray source and the quality of the detector. It generally applies that an optimally small focal size and simultaneously high photon flow advantageously influence the image quality. In CT, limits for the x-ray tube are additionally caused by its mounting in a rotating gantry with regard to cooling, weight and spatial expanse. Similar requirements also apply to stationary x-ray tubes that are used in the commercial field. In spite of an optimally small focus, an optimal x-ray tube should thus allow a high photon flow, and the efficiency should be as high as possible so that an optimally high photon flow can be achieved within the limits of the possible cooling of the anode.

In x-ray tubes used in the manner typical today, a high-energy electron beam is generated that strikes a rotating, massive anode and thereby generates x-ray radiation that is emitted in the form of bremsstrahlung and characteristic radiation from the surface of the anode. The efficiency of this type of x-ray generation typically lies in the range of <1%. In order to nevertheless generate a high photon flow, a high current density must be applied to the anode, which in turn results in a severe heating of the anode and in the extreme case to melting (i.e. to destruction) of the anode. In order to increase the power of such an anode, the heat must be better distributed and dissipated, meaning that—given the rotation anodes typical today—these must rotate more quickly and simultaneously be efficiently cooled.

For example, a transmission x-ray tube in which the x-ray generation is generated by an electron beam that strikes the front side of a thin anode is known from U.S. Pat. No. 7,180,981. The arising radiation is thereby emitted with high intensity at the back side of the thin anode, for the most part in a directed manner. The efficiency of such a transmission x-ray tube is higher by approximately a factor 10 than in a conventional x-ray tube with massive anodes. This is due to the fact that the bremsstrahlung portion of the arising x-ray radiation is increasingly emitted in the forward direction with increasing energy of the incident electrons. The characteristic radiation is simultaneously isotropically distributed in space. It is thus particularly advantageous to use the spatial portion of a generated x-ray radiation (consisting of the characteristic portion and the bremsstrahlung portion) in which the bremsstrahlung portion is optimally large in order to achieve an optimally high efficiency.

A problem of such x-ray tubes with a transmission anode is that the absolute generable photon flow is relatively small since the thin anode cannot be cooled, and therefore can generate x-ray radiation with only a very slight electron flow without destroying the anode.

As noted above, an x-ray tube in which a thin foil anode is used that is cooled at its back side with the aid of a liquid flowing past it is known from United States Patent Application Publication 2006/0115051. With this arrangement it is possible to increase the electron flow to the anode so that the photon flow of the emitted x-ray radiation that can be generated in total can be increased. A disadvantage of this arrangement is that, due to the design of the x-ray tube, only the backwardly directed x-ray radiation (thus essentially characteristic x-ray radiation) is available as usable radiation, so the efficiency of this x-ray tube is severely reduced.

In the x-ray tube according to the invention, an electron beam strikes the front side of a thin anode, and a coolant fluid is directed past the back side of the anode and the useful x-ray radiation exits from the x-ray tube through the coolant fluid. Since the x-ray tube is operated with relatively high voltage, the attenuation upon passage through the coolant turns out to be relatively small, such that a very high efficiency of the x-ray tube can be achieved, and at the same time a high absolute photon flow can be produced without the anode being damaged. The x-ray tube according to the invention is thus an x-ray tube wherein the coolant fluid is directed past the back side of the transmission anode so the usable radiation exits outwardly through the coolant fluid.

An x-ray tube designed with a relatively long anode path is advantageous here, so the incident electron beam does not always strike a single point but rather is distributed over a larger area so that a significant spatial distribution of the energy of the incident electron beam is additionally produced.

Corresponding to this basic idea described above, the x-ray tube according to the preamble has an anode fashioned as a transmission anode, with the transmission anode arranged between the vacuum region and the cooling channel, and the cooling channel is arranged between the transmission anode and the exit window, with the useful x-ray radiation exiting through the coolant.

According to the invention, this x-ray tube can be designed so that the transmission anode is fashioned annularly, for example in the form of a circular ring, a truncated hollow cylinder, or a hollow frustum.

The cathode can likewise be fashioned annularly, for example in the form of a circular ring, a truncated hollow cylinder, or a hollow frustum.

The cathode can be executed such that it can be activated in segments or at points. Alternatively, a laser can be provided to activate the cathode. For example, a passage window for a laser beam into the x-ray tube can be provided for activation of the cathode, or the cathode can be part of the outer wall of the vacuum region so that the cathode is excited on the back side by a laser beam in order to emit electrons on the front side thereof inside the x-ray tube.

The x-ray tube can be at least partially constructed from ceramic material so that appropriate insulation is ensured, in particular between the cathode and the anode.

Given use of a laser, this can be stationary relative to the anode, with a controlled optical deflection of the laser beam being provided.

As an alternative, the laser and the anode can be executed such that they can rotate relative to one another, with either the laser or the anode being stationary.

Water or an oleaginous substance can be used as a coolant, for example. It is particularly advantageous if the coolant is a material with an optimally low atomic number in order to keep the attenuation of the x-ray radiation as low as possible.

Furthermore, it is particularly advantageous for the cooling channel to be designed such that it is narrowed in the region of the transmission anode so that on the one hand the coolant that is to be transversed by the x-ray radiation in this region is optimally thin, and an optimally rapid flow of the coolant also occurs in this region in order to ensure as optimal a heat transport as possible.

In addition to the x-ray tube itself, the invention encompasses an x-ray system and a computed tomography system having an x-ray tube with the aforementioned features.

BRIEF DESCRIPTION OF THE DRAWINGS

FIG. 3 shows a CT system with x-ray tube according to the invention.

FIG. 4 shows a projection x-ray system with an x-ray tube with a transmission anode.

DESCRIPTION OF THE PREFERRED EMBODIMENTS

Figure 1:
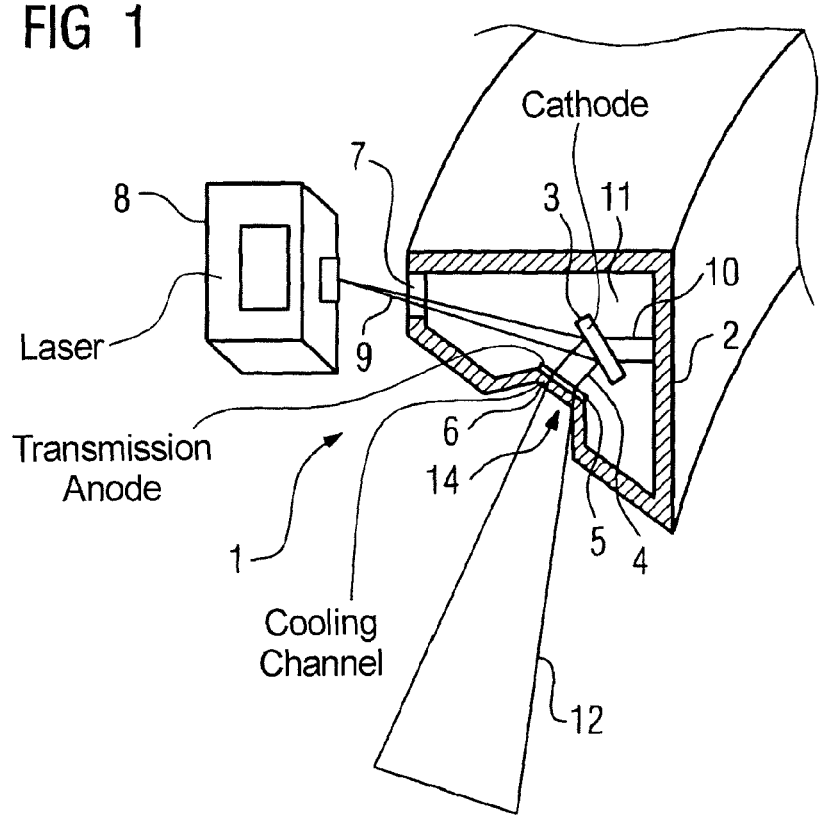
FIG. 1 shows an x-ray tube with transmission anode and laser-induced cathode on the electron emission side.

FIG. 1 shows a cross-section through an annularly designed x-ray tube 1 with a housing 2 and an optical window which enables a laser beam 9 (via a laser 8) to be applied on a cathode 3 fashioned as a frustum. The cathode 3 is connected with the housing 2 via a cathode mount 10 that is executed so as to be insulated. An electron emission that generates an electron beam 4 that strikes a transmission anode 5 arises at desired points due to the laser excitation. The transmission anode 5 is contacted by a cooling channel 6 (in which a coolant flows) on the side opposite the impact point of the electrons, such that the heat generated in the transmission anode 5 is dissipated. The x-ray radiation generated by the electron beam is limited by the transmission anode and by the cooling channel filled with coolant, which x-ray radiation is externally demarcated by an exit window 14, emitted outwardly and is available as useful (usable) x-ray radiation 12.

Figure 2:
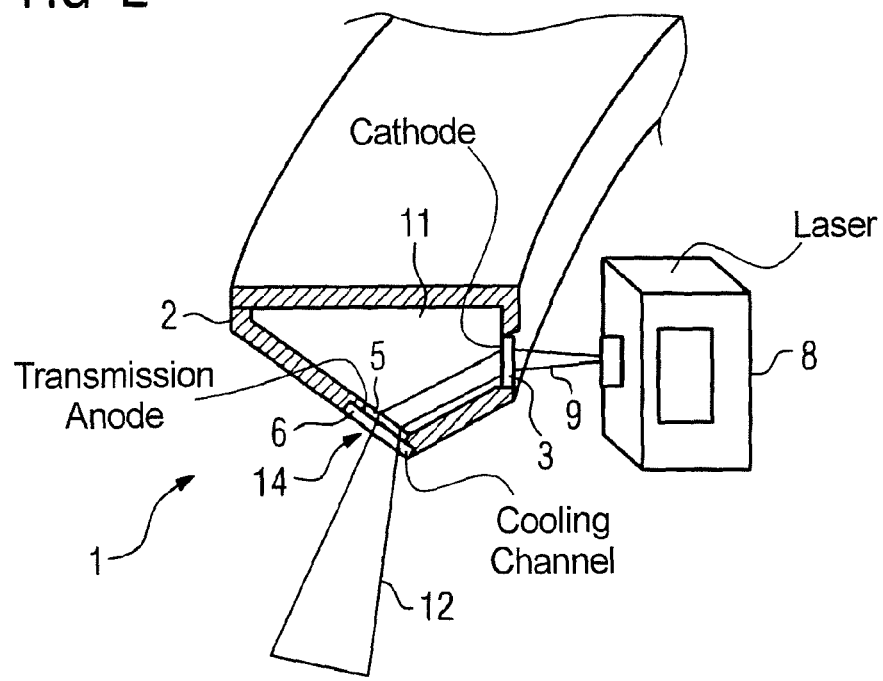
FIG. 2 shows an x-ray tube with transmission anode and laser-induced cathode on the side facing away from the electron emission.

A similar embodiment of an x-ray tube is shown in FIG. 2, wherein an optical window is foregone, and the cathode 3 is excited to electron emission from the back side by a laser that emits a laser beam 9, such that here as well an electron beam 4 is produced that strikes a transmission anode 5 and generates x-ray radiation. This x-ray radiation is radiated outward on the opposite side of the transmission anode 5 through a cooling channel 6 and an exit window 14 arranged there.

The x-ray tube is shown only schematically in two FIGS. 1 and 2. It is possible for the x-ray tube itself to rotate and, given a stationary laser, to distribute the heat arising at the focus over the length of the anode and the cooling channel through the rotation of the x-ray tube. The possibility also exists to use a stationary x-ray tube of an annular design, wherein the laser rotates along the circumference of the x-ray tube and generates at its position an emission spot on the cathode 3 (likewise of annular design). This x-ray tube can be used, for example, in a computed tomography system in this embodiment, with only the laser having to be arranged on the rotating gantry. Alternatively, a stationary laser and a stationary x-ray tube can be used, with the laser beam being positioned by appropriately aligned mirrors.

FIG. 3 shows such a computed tomography system with a stationary x-ray tube 1 and a laser system 8 with an optical deflection device 13 which deflects a laser beam 9 in an arbitrary manner to various points along the cathode 3 (arranged in a circle). Electron emission is excited on the opposite side at the impact points of the laser beam 9, such that an electron beam 4 is produced that generates on the transmission anode a focus at which x-ray radiation arises that can exit outwardly through the coolant located in the cooling channel 6 and be used as usable radiation 12.

In the example shown here, x-ray radiation can be generated at one or more points of the annularly arranged x-ray tube, corresponding to the mode of application of the computed tomography system, such that the absorption of a patient or another subject located on a patient bed 16 can be measured from a number of projection angles with the use of a detector 17 (likewise annularly arranged).

Another alternative to the apparatus of an x-ray tube according to the invention is shown in FIG. 4. This shows a projective x-ray system in which a focus is generated at a spatially fixed position, with the x-ray tube 1 itself being mounted such that it can rotate. The generation of the focus in turn occurs with a laser 8 with a laser beam 9 of fixed spatial orientation that also strikes the cathode and generates an electron emission that produces an electron beam, and therefore a focus on the transmission anode. In order to be able to operate this x-ray system with sufficient dose, the x-ray tube 1 is rotated quickly so that the focus distributed over a larger area of the transmission cathode 5 where it is also simultaneously cooled by the coolant flowing past. A spatially fixed focus from which the usable radiation 12 arises is created in this way, which focus can be used with the aid of a flat panel detector 17 in order to expose a patient or to generate corresponding projective x-ray exposures. Alternatively, such an x-ray tube can also be used in a C-arm system in order to generate tomographic exposures.

The shown examples merely describe a selection of the possible variations of the x-ray tube designed according to the invention. In particular, the generation of the electron beam can ensue not only induced by a laser but also by segmented and electronically activated cold cathodes. Moreover, an electron beam that is generated in a directed manner can be used with which the transmission anode is directly irradiated at an arbitrary point.

Multiple anode materials can be used (possibly in combination) in order to generate different energy spectra of the x-ray radiation so that the x-ray tube described herein is also usable in applications known as "dual energy" applications or "multi energy" applications.

Overall, an x-ray tube with increased efficiency and simultaneously high photon yield is provided by the x-ray tube according to the invention, which can be used both for the application in the computed tomography field and in the field of projective imaging.

Although modifications and changes may be suggested by those skilled in the art, it is the intention of the inventors to embody within the patent warranted hereon all changes and modifications as reasonably and properly come within the scope of his contribution to the art.

We claim as our invention:

1. An x-ray tube comprising:
   a tube housing;
   a cathode at said tube housing, said cathode comprising an optically activatable material that, when optically activated, emits electrons into an interior of said tube housing;
   a laser that emits a laser beam onto said cathode to optically activate said cathode;
   said tube housing comprising an outer wall surrounding an evacuated region, and said cathode forming a portion of said outer wall having a cathode exterior at an exterior of said outer wall, and said laser being disposed outside of said tube housing and emitting said laser beam onto said cathode exterior;
   a transmission anode in said tube housing toward which said electrons emitted by said cathode are accelerated to strike said anode to cause x-ray radiation to be emitted by said anode, said x-ray radiation including useable x-rays;
   a cooling channel having coolant filling therein in thermal communication with said transmission anode to cool said transmission anode;
   an evacuated region in said tube housing between said cathode and said transmission anode;
   said tube housing having an exit window therein through which said useable x-rays exit from said tube housing; and
   said transmission anode being disposed in said tube housing between said evacuated region and said cooling channel, and said cooling channel being disposed in said tube housing between said transmission anode and said exit window with said useable x-rays passing through said coolant toward said exit window.

2. An x-ray tube as claimed in claim 1 wherein said transmission anode has an annular shape.

3. An x-ray tube as claimed in claim 2 wherein said transmission anode is a circular ring.

4. An x-ray tube as claimed in claim 1 wherein said cathode has an annular shape.

5. An x-ray tube as claimed in claim 4 wherein said cathode is a circular ring.

6. An x-ray tube as claimed in claim 1 wherein said cathode comprises a plurality of discrete electron emission sites that are individually activatable to cause electrons to be emitted therefrom.

7. An x-ray tube as claimed in claim 1 wherein said laser and said transmission anode are stationary relative to each other, and comprising an optical deflector that deflects said laser beam onto said cathode exterior.

8. An x-ray tube as claimed in claim 1 wherein one of said laser and said transmission anode is rotatable relative to the other.

9. An x-ray tube as claimed in claim 8 wherein said laser is stationary.

10. An x-ray tube as claimed in claim 8 wherein said transmission anode is stationary.

11. An x-ray tube as claimed in claim 1 wherein said tube housing is at least partially comprised of ceramic material.

12. An x-ray tube as claimed in claim 1 wherein said coolant is water.

13. An x ray tube as claimed in claim 1 wherein said coolant is an oleaginous fluid.

14. An x-ray tube as claimed in claim 1 wherein said cooling channel has a first channel dimension in a region of said cooling channel beyond said transmission anode and a second channel dimension in a region of said cooling channel overlapping said transmission anode, said second channel dimension being substantially rust and said first channel dimension to allow passage of said useable x-rays therethrough with reduced attenuation of said useable x-rays.

15. An x-ray system for generating projection x-ray exposures, comprising:
   an x-ray tube comprising a tube housing, a cathode in said tube housing, said cathode comprising an optically activatable material that, when optically activated, emits electrons into an interior of said tube housing, a laser that emits a laser beam onto said cathode to optically activate said cathode, said tube housing comprising an outer wall surrounding an evacuated region, and said cathode forming a portion of said outer wall having a cathode exterior at an exterior of said outer wall, and said laser being disposed outside of said tube housing and emitting said laser beam onto said cathode exterior, a transmission anode in said tube housing toward which said electrons emitted by said cathode are accelerated to strike said anode to cause x-ray radiation to be emitted by said anode, said x-ray radiation including useable x-rays forming a projection beam, a cooling channel having coolant filling therein in thermal communication with said transmission anode to cool said transmission anode, an evacuated region in said tube housing between said cathode and said transmission anode, said tube housing having an exit window therein through which said useable x-rays exit from said tube housing, and said transmission anode being disposed in said tube housing between said evacuated region and said cooling channel, and said cooling channel being disposed in said tube housing between said transmission anode and said exit window with said useable x-rays passing through said coolant toward said exit window; and
   an x-ray detector spaced from said x-ray tube to allow placement of an examination subject between said radiation detector and said x-ray tube, said projection beam being incident on said detector after passage through said examination subject, and said detector generating a detector output representing an x-ray image of the examination subject from the projection beam incident thereon.

16. A computed tomography system comprising:
   a rotatable gantry;
   an x-ray tube mounted on said gantry for rotation therewith, said x-ray tube comprising a tube housing, a cathode in said tube housing, said cathode comprising an optically activatable material that, when optically activated, emits electrons into an interior of said tube housing, a laser that emits a laser beam onto said cathode to optically activate said cathode, said tube housing comprising an outer wall surrounding an evacuated region, and said cathode forming a portion of said outer wall having a cathode exterior at an exterior of said outer wall, and said laser being disposed outside of said tube housing and emitting said laser beam onto said cathode exterior, a transmission anode in said tube housing toward which said electrons emitted by said cathode are accelerated to strike said anode to cause x-ray radiation to be emitted by said anode, said x-ray radiation including useable x-rays forming a projection beam, a cooling channel having coolant filling therein in thermal communication with said transmission anode to cool said transmission anode, an evacuated region in said tube housing between said cathode and said transmission anode, said tube housing having an exit window therein through which said useable x-rays exit from said tube housing, and said transmission anode being disposed in said tube housing between said evacuated region and said cooling channel, and said cooling channel being disposed in said tube housing between said transmission anode and said exit window with said useable x-rays passing through said coolant toward said exit window; and an x-ray detector mounted on said gantry for rotation therewith spaced from said x-ray tube to allow placement of an examination subject between said radiation detector and said x-ray tube, said projection beam being incident on said detector after passage through said examination subject from a number of different projection angles during rotation of said gantry, and said detector generating a detector output representing projection data of the examination subject at each of the projection angles.

* * * * *